United States Patent [19]

Williams et al.

[11] Patent Number: 4,860,331
[45] Date of Patent: Aug. 22, 1989

[54] IMAGE MARKER DEVICE

[76] Inventors: John F. Williams, 4045 N. Oracle Rd., Apt. 237; Jerry D. Alexander, 4045 N. Oracle Rd., Apt. 258, both of Tucson, Ariz. 85705

[21] Appl. No.: 242,814

[22] Filed: Sep. 12, 1988

[51] Int. Cl.[4] .............................................. A61B 17/00
[52] U.S. Cl. .................. 378/163; 128/303 B; 116/278; 116/DIG. 14; 33/512
[58] Field of Search ............... 33/137 R, 483, 493, 33/494; 40/300, 586, 594; 116/278, DIG. 14; 128/653, 303 B; 378/20, 205, 163, 165

[56] References Cited

U.S. PATENT DOCUMENTS

| 2,293,324 | 8/1942 | Vladeff | 378/205 |
| 3,812,842 | 5/1974 | Rodriguez | 378/163 |
| 3,836,776 | 9/1974 | Gullekson | 378/163 |
| 3,867,634 | 2/1975 | Hounsfield | 378/20 |
| 4,005,527 | 2/1977 | Wilson et al. | 378/163 |
| 4,319,136 | 3/1982 | Jinkins | 378/163 |
| 4,506,676 | 3/1985 | Duska | 378/165 |
| 4,583,538 | 4/1986 | Onik et al. | 378/20 |

FOREIGN PATENT DOCUMENTS

| 205217 | 1/1968 | U.S.S.R. | 33/494 |
| 685278 | 9/1979 | U.S.S.R. | 378/163 |

OTHER PUBLICATIONS

New Inventions article, "A Trephine Needle for Vertebral Body Biopsy" 2/27/60.

Primary Examiner—William A. Cuchlinski, Jr.
Assistant Examiner—Jeffrey J. Hohenshell
Attorney, Agent, or Firm—Oldham & Oldham Co.

[57] ABSTRACT

A marker device for body scanning which permits the location of internal parts of a patient's body by reference to image reference points produced by marks on the device attached to the surface of the patient's skin during the scanning process. The device comprises a flexible tape which includes a substrate with marks, usually lines, thereon, the substrate being relatively transparent to the scanning waves, while the reference lines are relatively opaque with respect thereto. The substrate is conveniently formed from plastic, while the reference lines are advantageously metallic in character, preferably copper strips. The substrate is ordinarily coated with a pressure sensitive adhesive to allow its attachment to the patients outer skin, and it may be perforated with holes to accommodate insertion of biopsy needles.

14 Claims, 1 Drawing Sheet

IMAGE MARKER DEVICE

TECHNICAL FIELD

This invention relates to the imposition of coordinate marks on fluoroscopic or film images produced during patient scanning procedures. More particularly, this invention relates to a marker device adapted for placement over the part of a patient's body to be examined by non-intrusive wave-imaging, which produces visual indexing marks on the body parts of clinical interest. Specifically, this invention relates to a tape comprising a flexible substrate coated with a pressure sensitive adhesive on one side thereof which contains indexing marks, advantageously substantially opaque to the scanning waves employed in the scanning procedure, which marks produce visible reference points superimposed on the image of the patient's body produced by the procedure.

BACKGROUND OF THE INVENTION

In recent years, advances in wave technology and detecting devices associated therewith have allowed physicians to examine organs and other internal body features of patients without resort to invasive procedures which unavoidably involve the risk of infection and trauma attendant to all surgery, even that of the simple diagnostic variety. By use of such technology, including magnetic resonance, positron emission, ultrasound, and similar techniques, in conjunction with wave detectors and data processing equipment, cross sections of the entire body are now readily obtainable. The advantages of the new diagnostic tools are so pronounced that most of the larger hospitals and similar facilities now have this equipment available for their staffs. Computerized axial tomography, for example, commonly known as CAT scan, once relatively exotic has now become common place, and such equipment is available for use throughout the country. Among the advantages of total body scanning may be mentioned the fact that the injection of radioisotopes is not required to produce a record of findings; it being possible to obtain images of tissue density across a complete cross section of the body being scanned without resort to such materials. The technique is particularly useful in visualizing the retroperitoneal space, for example, the pancreas, liver, spleen, and ovaries, as well as the abdominal section of the aeorta.

While such equipment has allowed physicians to view internal portions of the body previously inaccessible in the absence of surgery, one of the disadvantages of the equipment is the tendancy to over-expose patients to excessive amounts of wave energy during the scanning procedure. For example, in employing in such techniques, it is frequently necessary to provide a reference point relative to which internal features of the patient may be located, fluroscopically or on film, for subsequent biopsy, or for other purposes. Commonly such a reference point is established by placing a small piece of metal as a marker on the area of interest prior to exposing the patient to, for example, X-ray radiation. Quite often, however, after such placement and subsequent X-ray exposure, it is necessary to reposition the marker to make it more useful as a reference point. Such repositioning necessitates additional X-ray exposure, with still further adjustment and more X-ray exposures sometimes being found necessary. While small amounts of exposure to radiation are normally justified on a risk/benefit basis, X-ray exposures are cumulative and capable of producing adverse cellular changes, including malignancies, in tissue with which it comes in contact. Consequently, it is highly desirable to reduce exposure to such waves to the absolute minimum necessary to achieve the result desired.

DISCLOSURE OF THE INVENTION

In view of the preceding, therefore, it is a first aspect of this invention to provide a reference marker for use in the medical imaging procedures.

A second aspect of this invention is to provide an indexing reference useful in patient imaging diagnostic procedures which results in reduction of patient exposure time to the imaging scanning waves.

Another aspect of this invention is to provide an indexing tape which is attachable to a patient, and which superimposes reference marks on the internal image of the patient obtained during the scanning procedure.

A further aspect of this invention is to provide an imaging reference marking device that cannot be accidentally shifted or dislodged from the patient's skin over the area being scanned. An additional aspect of this invention is the provision of an imaging marker device which permits simultaneous indexing over a substantial portion of a patient's internal features.

Another aspect of this invention is to furnish an inexpensive, medical imaging reference marker that is easy to use and which is disposable.

The foregoing and still additional aspects of the invention are provided by a marker device for indexing internal features of medical patients during image-scanning procedures comprising a flexible tape adapted for attachment to the skin of a patient, said tape including a rectangular substrate with a plurality of index markings thereon, said markings and said substrate having detectably different affects on scanning waves striking the tape during the image-scanning of a patient.

The foregoing and other aspects of the invention are provided by a marker device for indexing internal features of medical patients during image-scanning procedures comprising a flexible plastic tape adapted for attachment to patients by means of a pressure sensitive adhesive disposed thereon, which includes a rectangular substrate with a plurality of index marking lines equidistant from each other and positioned at right angles to the longitudinal axis of said substrate, wherein said substrate is substantially permeable to scanning waves striking said tape, while said marking lines are substantially impermeable thereto.

BRIEF DESCRIPTION OF DRAWINGS

The invention will be better understood when reference had to the following drawings of the invention, in which like numbers refer to like parts and in which.

DESCRIPTION OF THE PREFERRED MODE OF THE INVENTION

Figure 1:
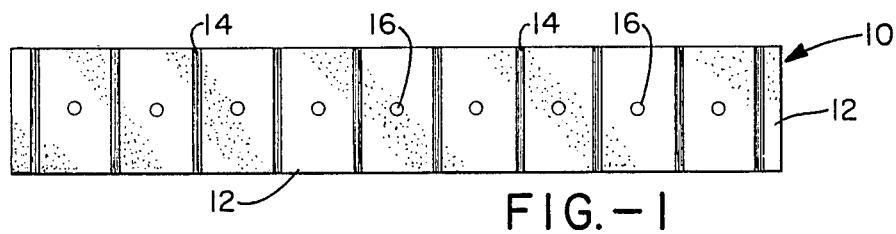
FIG. 1 is a plan view of the marker device of the invention.

FIG. 1 is a plan view of the marker device of the invention, generally 10. The device comprises a substrate 12 containing thereon scanning wave blocking strips 14. The substrate may also be provided with biopsy access holes 16, located between the blocking strips, the spacing between strips depending upon the amount of imaging detail anticipated, as well as the accuracy required in locating such detail. In most instance, however, the blocking strips will be positioned from about 1½ centimeters to 2½ centimeters apart, a distance of about 2 centimeters apart being satisfactory in most cases.

The purpose of the tape 10 is to provide detectably different affects on the scanning waves striking the tape during the scanning of a patient so that the tape markings are distinguishable on the scanning image produced, enabling the internal features of the patient's body over which the tape is placed to be located relative to the image of the markings superimposed thereover. This is best achieved by selecting substrates which are relatively permeable to the scanning waves, and marker strips which are relatively impermeable thereto, advantageously strips which substantially block the waves.

Accordingly, the substrate will be selected from any permeable material, particularly from those permeable to X-rays such as fabric, plastic, and the like, reinforced fiber glass epoxy materials being especially preferred since besides being permeable to X-rays, tapes made from such materials are both strong and sufficiently flexible to be contoured over the surface of the patient's skin. Other plastics could also be used, however, such as PVC, polyethylene, polypropylene, polyesters, and others.

Substantial wave opacity, on the other hand, is desired for fabricating the scanning wave blocking strips 14. Consequently, it is preferred that such strips be made from thin metal, plastic, inks containing metal, or similar materials. It has been found, however, that the use of copper strips results in a sharply defined image, and the use of copper is, therefore, preferred for use with the invention. Where the strips consist of metal, they can be fastened on one or both sides of the substrate, for example, with a suitable adhesive. In one process, sheets of thin copper are adhesively fastened to both sides of a fiber glass reinforced epoxy film, following which the portion of the sheets destined to form the blocking strips are covered with a protective ink or film. The sheets are than exposed to ammonia, and thereafter immersed in a treatment solution which dissolves the ammonia exposed portions, leaving only the protected marker strips behind fastened to the substrate. The sheet is than slit to form tapes of the desired size in ways well known to the art.

The dimensions of the tape may be varied within wide limits; however, typically, tapes of from about 8 to 14 inches long are convenient to use, particularly when the width of the tape is from about ¾ inch to 1½ inches wide. The thickness of the substrate will depend upon the strength of the material from which it is fabricated, as well as its permeability. In the case of a fiber glass reinforced epoxy material, it has been found that a substrate of from about 2 to 8 microns will result in tape of adequate strength, flexible enough to follow the contours of the skin of the patient on which it is placed, and will provide good X-ray permeability characteristics.

The dimensions of the scanning wave blocking strips may also be varied within fairly broad limits; however, in the case of copper, an over-all thickness of from about 0.003 inch to 0.006 inch will provide sufficient X-ray impermeability and sharp definition to allow precise indexing of the patient. Such thickness may be provided with two strips, one positioned over the other on either side of the substrate, or in a single strip on one side of the substrate. The width of the strip will conveniently be from about 1/16 inch to ⅛ inch.

Figure 1A:
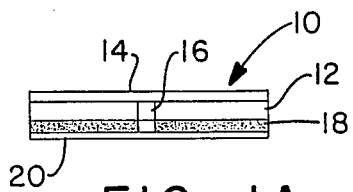
FIG. 1A is an end view of the marker device of FIG. 1.

FIG. 1A is an end view of the marker device 10 of FIG. 1 showing further details of the substrate 12 on which a scanning wave blocking strip 14 is located. The bottom of the tape laminate is coated with a pressure sensitive adhesive film 18, protected by a backing strip 20 until used, at which time the latter strip is peeled from the tape. A biopsy access hole 16 is provided, as shown.

While not required by the marker device, the provision of biopsy holes 16 between the blocking strips 14 allows biopsy needles to be precisely inserted through the tape into the patient, and desired biopsy samples removed, as required. While one round hole is shown in FIG. 1 between each pair of adjacents strips, more holes can be provided if required, and holes with other than round shapes may be used. Although larger or smaller holes may be employed, the use of round holes having a diameter of about ⅛ inch will accommodate most biopsy needles.

Figure 2:
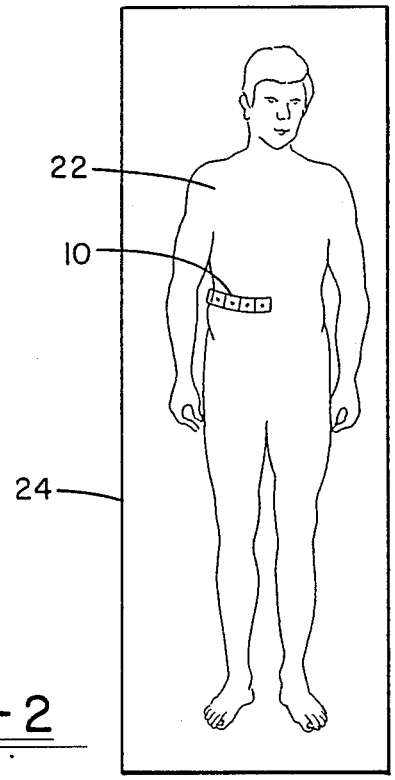
FIG. 2 shows a patient lying on a stretcher wearing a marker device of the invention over an area of the body of clinical interest, preparatory to being scanned.

FIG. 2 shows a patient 22 lying on a stretcher 24 wearing a marker device 10 of the invention over the area of the body of clinical interest, preparatory to being scanned. The marker device 10 is fastened to the patient's skin by means of a pressure sensitive adhesive coated over all, or a portion of the skin-side of the device. The pressure sensitive adhesive may be any of those known to the art including pressure sensitive adhesives of the acrylate or elastomeric types. While the time of contact with the patient's skin is relatively brief, it is desirable that the adhesive be of a hypo-allergenic type so that irritation to the patient's skin can be avoided.

Figure 3:
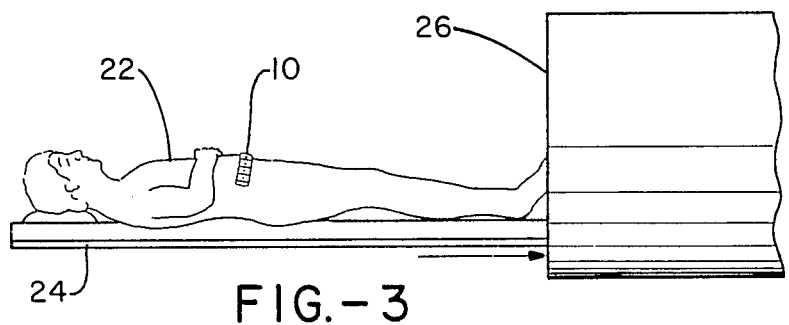
FIG. 3 is a representation of a patient about to be inserted into an image-generating scanning device.

FIG. 3 is a representation of a patient about to be inserted into an image-generating scanning device. As illustrated, the patient 22, lying on a stretcher 24 is about to be passed into a scanning device 26 in the direction of the associated arrow. The patient has a marker device 10 attached to his body by means of the pressure sensitive adhesive, as previously described in connection with FIG. 2. While the invention is of particular usefulness in connection with computerized axial tomography, it also has application to various other scanning techniques including ultra-sound and similar techniques.

Figure 4:
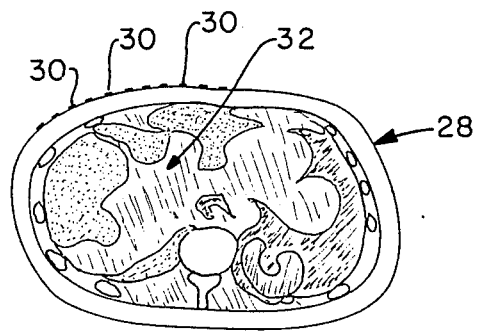
FIG. 4 illustrates a transverse cross section of a patient's body to which a marker device of the invention has been attached.

FIG. 4 illustrates a transverse cross section of a patient's body, generally 28, to which a marker device of the invention has been attached. The relative impermeability of the scanning wave blocking strips 14 produces discernable marks 30 on the scanning image obtained. The position of the marks relative to the internal features, generally 32, allows the position of such features to be ascertained simply by noting their location with respect to a particular mark. With the location thus ascertained, a biopsy needle can be inserted through an appropriate biopsy hole 16, and a sample of the tissue of interest obtained. Commonly, as shown in FIG. 1, the scanning wave blocking strips are located at equal distances from each other. Other positioning may be choosen, however, and markings other than lines may be employed such as dots or other shapes.

While in accordance with the patent statures the best mode and preferred embodiment of the invention has been described, it is to be understood that the invention is not limited thereto, but rather is to be measured by the scope and spirit of the appended claims.

What is claimed is:

1. A marking device for indexing internal features of medical patients during image-scanning procedures comprising a flexible tape adapted for attachment to the skin of a patient, said tape including a rectangular substrate with a plurality of index markings thereon, and with perforated biopsy access holes between each pair of adjacent index marks therein, said markings and said substrate having detectably different affects on scanning waves striking the tape during the image-scanning of a patient.

2. A marker device according to claim 1 wherein said substrate is substantially permeable to said scanning waves, and said markings are substantially impermeable to said scanning waves.

3. A marker device according to claim 2 wherein said substrate is a flexible plastic strip and said markings include a metallic constituent.

4. A marker device according to claim 3 in which said markings are configured in the shape of lines equidistant from with each other, positioned at right angles to the longitudinal axis of said substrate.

5. A marker device according to claim 4 wherein said substrate is perforated with at least one hole between each adjacent pair of marking lines.

6. A marker device according to claim 1 wherein said attachment is achieved by a pressure sensitive adhesive disposed on said substrate.

7. A marker device for indexing internal features of medical patients during image-scanning procedures comprising a flexible plastic tape adapted for attachment to patients by means of a pressure sensitive adhesive located thereon, said tape including a rectangular substrate with a plurality of index marking lines equidistant from each other and positioned at right angles to the longitudinal axis of said substrate, and with perforated biopsy access holes between each pair of adjacent index markings therein, wherein said substrate is substantially permeable to scanning wave striking said tape, while said marking lines are substantially impermeable thereto.

8. A marker device according to claim 7 in which said marking lines comprise strips of metal attached to said substrate.

9. A marker device according to claim 8 wherein said metal is copper.

10. A marker device according to claim 9 wherein said substrate is perforated with at least one hole between each adjacent pair of marking lines.

11. A marker device for indexing internal features of medical patients during image-scanning procedures comprising a flexible plastic tape adapted for attachment to patients, said tape including a rectangular substrate with a plurality of index marking lines and perforated biopsy access holes wherein said index marking lines are equidistant from each other and positioned at right angles to the longitudinal axis of said substrate, and wherein said perforations are between each pair of adjacent index marks on said substrate, wherein said substrate is substantially permeable to scanning waves striking said tape, while said marking lines are substantially impermeable thereto.

12. A marker device according to claim 11 in which said marking lines comprise strips of metal attached to said substrate.

13. A marker device according to claim 11 wherein said metal is copper.

14. A marker device according to claim 11 wherein said substrate is perforated with at least one hole between each adjacent pair of marking lines.

* * * * *